United States Patent [19]

Gebhart et al.

[11] 4,174,180
[45] Nov. 13, 1979

[54] ULTRAMICROSCOPIC SPECTROMETER

[75] Inventors: Josef Gebhart, Dietzenbach; Gerhard Heigwer, Offenbach am Main; Joachim Heyder; Friedel Haas, both of Frankfurt am Main; Christa Roth, Eschborn, all of Fed. Rep. of Germany

[73] Assignee: Gesellschaft fur Strahlen- und Umweltforschung mbH, Munchen, Neuherberg, Fed. Rep. of Germany

[21] Appl. No.: 823,936

[22] Filed: Aug. 11, 1977
(Under 37 CFR 1.47)

[30] Foreign Application Priority Data

Aug. 19, 1976 [DE] Fed. Rep. of Germany ....... 2637333

[51] Int. Cl.² ............................................ G01N 21/00
[52] U.S. Cl. .................................... 356/338; 356/246
[58] Field of Search ............... 356/103, 246, 338, 339, 356/340

[56] References Cited

U.S. PATENT DOCUMENTS

| | | | |
|---|---|---|---|
| 2,909,960 | 10/1959 | Orr, Jr. et al. | 356/103 |
| 3,398,286 | 8/1968 | Ford et al. | 356/103 X |
| 3,785,735 | 1/1974 | Friedman et al. | 356/103 X |

Primary Examiner—John K. Corbin
Assistant Examiner—Matthew W. Koren

Attorney, Agent, or Firm—Spencer & Kaye

[57] ABSTRACT

An ultramicroscopic spectrometer for examining properties of aerosol particles includes a receptacle having a wall defining a measuring chamber; an aerosol jet generating arrangement for forming an aerosol jet from the particles by aerodynamic focusing; a mount supporting the aerosol generating arrangement in the measuring chamber; a first passage in the receptacle wall for passing an incident illuminating beam through the receptacle wall into the measuring chamber; and a second passage in the receptacle wall for passing an information beam respectively an observation beam of the aerosol jet through the receptacle wall from the measuring chamber. The axes of the illuminating beam, the information beam and the aerosol jet intersect in a measuring field. The spectrometer further has a mount adjusting device arranged adjacent the receptacle base externally of the meauring chamber; a first coupling arrangement extending through an opening in the base and connecting the mount with the mount adjusting device and sealing the opening airtight; an astigmatic image forming system supported in the first passage for focusing the illuminating beam in a measuring field; and an adjusting-and-sealing assembly operatively connected to the second passage and displaceably coupled with the receptacle.

1 Claim, 2 Drawing Figures

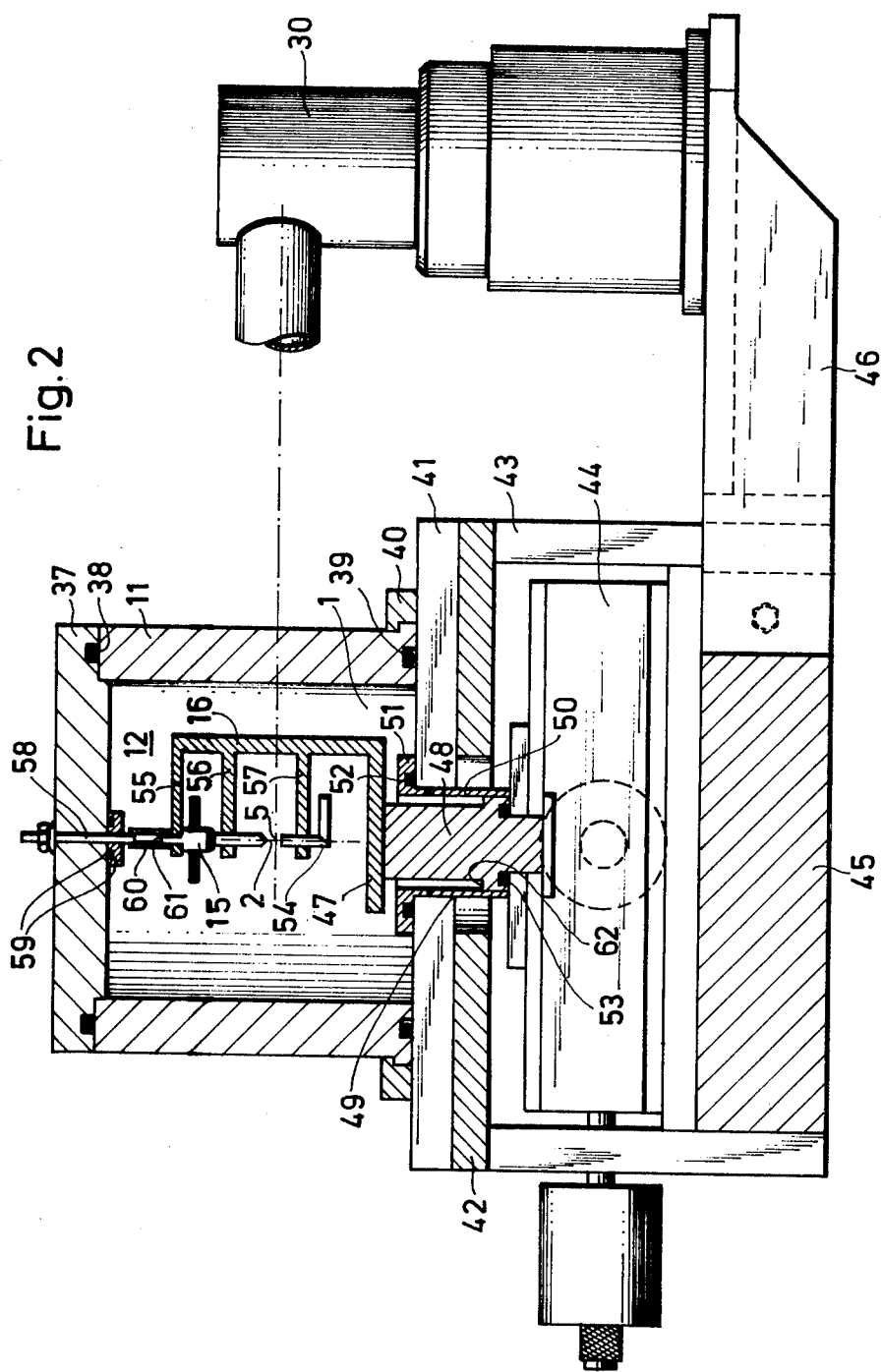

ULTRAMICROSCOPIC SPECTROMETER

BACKGROUND OF THE INVENTION

This invention relates to an ultramicroscopic spectrometer for determining the size, concentration and index of refraction of aerosol particles which are aerodynamically focused into an aerosol jet by an aerosol jet generating system. The spectrometer is arranged by means of a mount within a receptacle, the wall of which has a first passage for the incident illuminating beam and a second passage for the information beam of the aerosol jet. The axes of the illuminating beam, the information beam and the aerosol jet intersect in a measuring field.

The aerosol particles contained in the environmental atmosphere have particle diameters spanning a range of many orders of size. An important size range within atmospheric physics and industrial hygiene is constituted by submicroscopic aerosol particles.

The classical processes for the analysis of particle magnitudes comprise the separation of particles onto a proper specimen carrier and a subsequent evaluation of the specimen by a light microscope or an electron microscope. These processes are very time consuming due to a visual counting of the particles. Further, the light microscope must be generally considered unsuitable for the submicroscopic particle range, since the formation of sharp images of the particles below the wavelength of light is not possible.

For the above reasons the ultramicroscopic process was developed for particles whose image could not be sharply reproduced. The ultramicroscopic process determines the particle size not by measuring the dimension of the particle image, but by measuring the intensity of the scattered radiation. The use of light scattering for size determination is particularly advantageous in case of ultramicroscopic particles (whose diameter is smaller than the wavelength of the light used), because the intensity of the scattered light in this order of size increases in a direct proportion (that is, it increases monotonically) with the particle size. This unequivocal relationship between scattered light intensity and particle diameter exists for both monochromatic light and white light.

Further, particles which are formed of materials with different real components of the index of refraction differ in their scattered light intensity by a constant factor which is independent from the particle diameter and which may be correlated unequivocally with the index of refraction. The influence of the self-absorption of the particles (complex index of refraction) on the light scattering is, in this size range, substantially negligible. Particles which deviate from the spherical shape are, in the light scattering, associated with the diameter of a sphere which has the same volume as the non-spherical particles.

In a conventional arrangement, however, ultramicroscopy can utilize the properties of light scattering (which are advantageous for the size determination) only in a limited manner, since the background scattering of the specimen carrier significantly restricts the lower limit of detection sensitivity and further, the conventional examining arrangement does not allow a substantial automation of the evaluation.

On the other hand, for measuring the concentration and size of aerosol particles, apparatuses are known which operate on the basis of light scattering and are known as optical particle counters. In this connection reference is made to A. E. Martens and K. H. Fuss, in the Journal *"Staub-Reinhaltung der Luft,"* Vol. 28, p. 229 (1978). According to the process described in that publication, the particles are passed individually and sequentially through an optical gate, the scattered light flash emitted by each individual particle is photoelectrically recorded and the particle size is determined by the magnitude of the electric pulse. The measure for the concentration is the number of counting pulses per unit time. The advantages of an optical particle counter reside in the fact that the particles may be analyzed as they are carried by air and thus a preceding separation onto a specimen carrier need not be performed and further, based on the photoelectric recording of the light flashes, a high-grade automation may be effected.

In their present state of development, however, the optical particle counters have a number of disadvantages. Thus, by using conventional incandescent lamps as light sources and because of imprecise optical beam guidances, the scattered light intensity is too weak or the background scattering is too high for individually sensing particles that have a size below the wavelength of light. The principal measuring range of these apparatuses is thus above the wavelength of light.

For particle sizes above the wavelength of light the relationship between the scattered light intensity and the particle diameter is not unequivocal when monochromatic light is used. Thus, white light and a special scattered light angle range has to be selected to obtain an unequivocal, monotonously increasing calibration curve in a predetermined range of particle size.

Further, in optical particle counters used heretofore little attention has been given to the preparation of the illuminating beam and the guidance of the aerosol through the measuring field. The result has been a small resolving power of these apparatuses. For particle sizes above the wavelength of light, the light scattering is not a volume phenomenon but a surface phenomenon. Thus, the influence of the particle shape on the results of measurement increases inasmuch as irregularly-shaped articles are no longer assigned the diameter of a sphere of the same volume.

SUMMARY OF THE INVENTION

It is an object of the invention to provide an improved ultramicroscopic spectrometer which ensures an intensive, homogeneous and constant illumination of the aerosol jet in the measuring field by means of externally effected, microscopically accurate adjustments of the aerosol jet and the information beam and by means of an optical shaping of the illuminating beam.

These objects and others to become apparent as the specification progresses, are accomplished by the invention, according to which, briefly stated, the ultramicroscopic spectrometer for examining properties of aerosol particles includes a receptacle having a wall defining a measuring chamber; an aerosol jet generating arrangement for forming an aerosol jet from the particles by aerodynamic focusing; a mount supporting the aerosol generating arrangement in the measuring chamber; a first passage in the receptacle wall for passing an incident illuminating beam through the receptacle wall into the measuring chamber; and a second passage in the receptacle wall for passing an information beam of the aerosol jet through the receptacle wall from the measuring chamber. The axes of the illuminating beam, the information beam and the aerosol jet intersect in a measuring field. The spectrometer further has a mount adjusting device arranged adjacent the receptacle base externally of the measuring chamber; a first coupling arrangement extending through an opening in the base and connecting the mount with the mount adjusting device and sealing the opening airtight; an astigmatic image forming system supported in the first passage for focusing the illuminating beam in a measuring field; and an adjusting-and-sealing assembly operatively connected to the second passage and displaceably coupled with the receptacle.

In accordance with a preferred embodiment of the invention, the mount has a lower web to which is secured a post which constitutes one part of the first coupling arrangement and which is fixedly attached to the mount adjusting device. The first coupling arrangement has a second part constituted by a flexible sealing sleeve which surrounds the post and which is attached by means of flanges to the bottom of the receptacle and the mount adjusting device.

According to a further feature of the invention, the astigmatic image forming system is constituted by a cylinder lens and an afterconnected spherical lens both supported in a tubular sleeve which, in turn, constitutes a component of the first passage.

In accordance with a further feature of the invention, a tube guiding the information beam is attached, with a microscope objective projecting into the receptacle, to the adjusting component of the adjusting-and-sealing assembly externally of the receptacle and further, the sealing component comprises a further flexible sleeve which is sealingly secured to the wall of the receptacle and the tube.

BRIEF DESCRIPTION OF THE DRAWINGS

FIG. 2 is a sectional view taken through the receptacle of the spectrometer according to the invention, in a plane perpendicular to the sectional plane of FIG. 1.

DESCRIPTION OF THE PREFERRED EMBODIMENT

Figure 1:
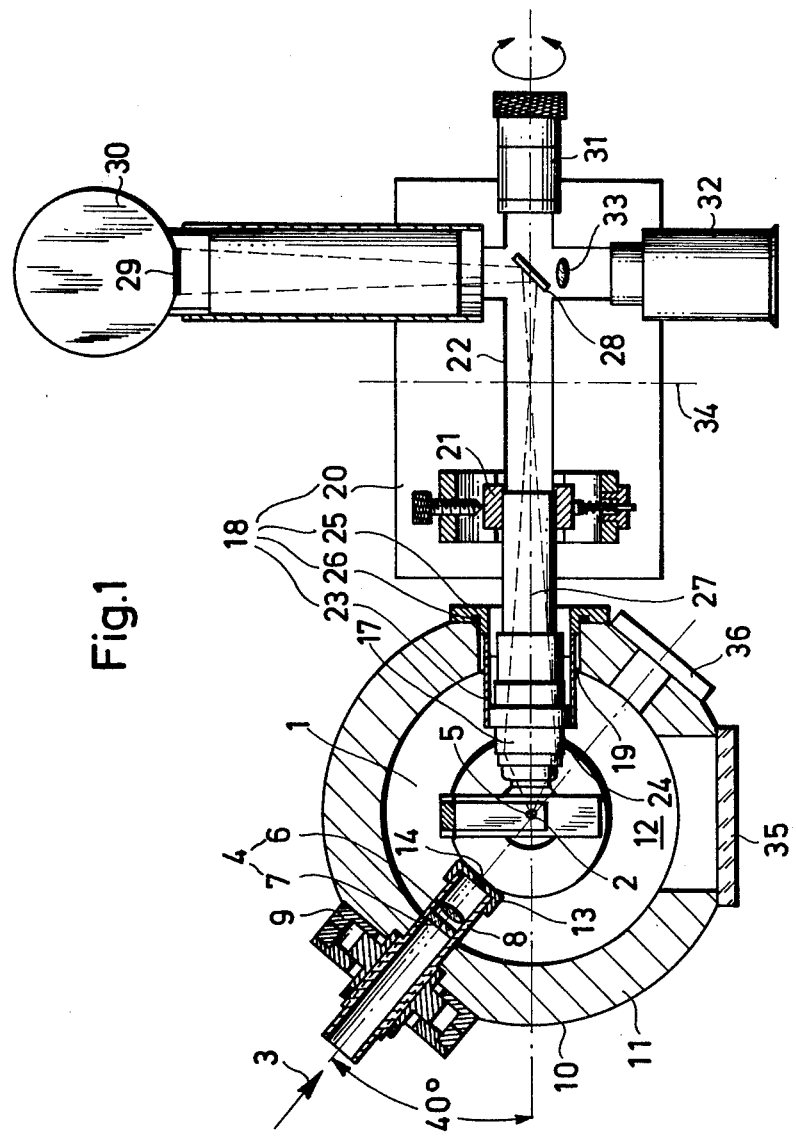
FIG. 1 is a sectional view of a spectrometer according to the invention taken in the plane of observation.

The optical structure of the aerosol spectrometer 1 is illustrated in FIG. 1 which shows a cross section of the apparatus through the plane of observation. A monochromatic laser light beam 3 serves for illuminating the aerosol jet 2 oriented perpendicularly to the plane of the drawing. The laser generating apparatus (which is not illustrated) is readily exchangeable so that the wavelength and power of the laser beam 3 may be varied as required. Because of its small beam divergence, the laser beam 3 may be focused (with the aid of an optical system described below) on a very small spot (of elliptical cross section). In this manner a small effective measuring volume 5 is obtained with a simultaneously high irradiation strength in the measuring field. A small measuring volume 5 which lies in the aerosol jet 2 is required for measurements in case of high particle concentrations, whereas a high irradiation strength leads to a high degree of sensitivity of response.

For focusing the laser beam 3 in the measuring volume 5 there is provided an astigmatic lens system 4 which is formed of a spherical lens 6 and a cylindrical lens 7. Both lenses are arranged in series as viewed in the direction of the laser beam 3 in a passage tube 8 which is sealingly secured to a flange 9 arranged on the outer wall 10 of the receptacle 11. The frontal terminus of the tube 8 projecting into the inner space 12 (measuring chamber) of the receptacle 11 is covered by a screen 13 having a diaphragm opening 14.

The aerosol jet 2 is generated by a nozzle system 15 which is secured to a mount 16. The nozzle system 15 will be described in more detail later in connection with FIG. 2.

The cross section of the laser beam 3 is elliptically shaped. The thin aerosol jet 2 is passed perpendicularly to the laser beam 3 and the major axis of the ellipse. The aerosol jet 2 is set in such a manner that it penetrates the elliptical cross section of the laser beam in its center. The minor axis of the ellipse is determined by the focal length of the spherical lens 6. The minor axis delimits that portion of the aerosol jet 2 which is illuminated by the laser beam 3 and thus bounds the height of the effective measuring volume 5. The length of the major axis depends upon the position and the focal length of the cylinder lens 7. The ratio of the diameter of the aerosol jet 2 to the length of the major axis of the ellipse determines the homogeneity of the illumination of the measuring field and thus determines the resolving power of the spectrometer 1. A laser beam of an elliptical cross section having a minor axis of 20 $\mu$ and a major axis of 150 $\mu$ has been experimentally found to be advantageous. The light scattered at the particles of the aerosol jet 2 is collected with the aid of a microscope objective 17 under a mean scattering angle of 40°. The primary laser beam 3 is absorbed in a light trap 36. The microscope objective 17, similarly to the tube 8, also projects into the inner space 12 of the receptacle 11 and is, by means of a sealing-and-adjusting unit 18, sealed with respect to an opening 19 provided in the wall 10 of the receptacle 11 and adjustable in its position with microscopic precision. The unit 18 comprises an adjusting device 20 formed of a three dimensional cross slide of known structure to which there is secured a passage tube 22 by means of a mount 21. The frontal terminus of the tube 22 carries the microscope objective 17. The sealing of the microscope objective 17 with respect to the receptacle 11 is effected by a sealing sleeve 23 which tightly surrounds a collar 24 of the microscope objective 17 and is affixed to the outer wall 10 of the receptacle 11 by means of a flange 25 with the interposition of an O-ring 26. The cross slide allows displacements parallel to the axis of tube 22 and two directions perpendicular to this axis.

The microscope objective 17 separates an information beam 27 from the measuring volume 5. The information beam 27 is constituted by the light scattered at the particles of the aerosol jet 2 in the measuring volume 5. The illuminating beam 3, the aerosol jet 2 and the information beam 27 and particularly the axes thereof, intersect in a single point in the measuring volume 5. Preferably, the illuminating beam 3 and the information beam 27 lie in a plane (observation plane) which is identical to the sectional plane of FIG. 1. The aerosol jet 2 penetrates the observation plane in a perpendicular orientation thereto.

The receiving unit for the information beam 27 includes a small mirror 28 which, dependent upon its angular positioning by means of a setscrew 31, deflects the beam 27 either towards the cathode 29 of a photomultiplier 30 including electronic evaluation circuitry or towards the ocular 32 through a lens 33 for visual observation. The microscope objective 17 reproduces the measuring field 5 in a plane 34 with exchangeable diaphragms (not shown). The receiving unit or, more particularly, the position of the passage tube 22 is adjusted by means of the cross slide 20 when the diaphragm edges and the aerosol jet 2 are seen sharply in the diaphragm center through the ocular 32.

For a direct observation of the inner space 12, the airtight receptacle 11 is provided with a window 35.

Turning now to FIG. 2, the spectrometer 1 is illustrated therein in a section taken in a plane which is oriented perpendicularly to the observation plane (that is, perpendicularly to the section plane of FIG. 1). The receptacle 11 consists of a cylindrical housing having a lid 37 which is sealingly secured to the upper edge face of the receptacle by means of an O-ring seal 38. The receptacle 11 is positioned on a base plate 41 and is secured thereto by a flange 40. An O-ring 39 positioned between the lower edge face of the receptacle 1 and the base plate 41 seals the measuring chamber 12. The base plate 41 is mounted on a cross table housing 43 by means of an intermediate insulating and damping member 42. The cross table housing 43 accommodates a further cross slide carriage 44 of conventional structure. The housing 43 is seated on an optical bench 45 on which there is arranged a mounting plate 46 having a height adjusting device for the photomultiplier 30.

Within the measuring chamber 12 of the receptacle 11 there is arranged the mount 16 for the nozzle 15 serving to guide the aerosol jet 2. The mount 16 is connected with the cross slide 44 by means of a socket portion 47 and a post 48 passing through an opening 49 provided in the base plate 41. The opening 49 is sealed by means of a sealing sleeve 50 entirely surrounding the post 48 and by means of a flange 51 and an O-ring 52 provided between the underside of the flange 51 and the upper face of the base plate 41. That end portion of the sealing sleeve 50 which is remote from its flange 51, circumferentially firmly engages a collar 62 of the post 48. The sealing of the post 48 with respect to the cross slide 44 is effected by an O-ring 53 arranged at the underside of the collar 62.

The mount 16 serves not only for securing the aerosol inlet nozzle 15, but also as a support for the aerosol outlet 54. The nozzle 15 is held by two arms 55 and 56 of the mount 16, whereas the outlet 54 is supported by an arm 57, also forming part of the mount 16. The aerosol feed pipe 58 passes through an opening in the lid 37 of the housing. At the inner face of the lid 37 the feed pipe 58 is surrounded by a seal 59. The feed pipe 58 is flexibly connected with the nozzle inlet 61 by a hose 60, so that the position of the nozzle mount 16 may be adjustable by means of the cross slide 44.

The sealing sleeve 23 for the microscope objective 17 as well as the sealing sleeve 50 for the post 48 need not necessarily project into the inner space 12 of the receptacle 11. They may terminate at the outer surface of the receptacle or, as the case may be, the base plate 41 without thereby adversely affecting the adjustability and the sealing of the sealing-and-adjusting unit 18 or the connecting members 48 and 50.

The aerosol is blown through the measuring field 5 with the aid of the nozzle 15 which is arranged perpendicularly to the laser beam 3 and the earlier-defined observation plane. In order to generate a thin aerosol jet 2 within the measuring volume 5, the aerosol stream is aerodynamically focused with the aid of a surrounding jacket formed of filtered air or helium. For this purpose, the aerosol is drawn through a capillary having a diameter of approximately 200 $\mu$. At the outlet of the capillary, the aerosol jet 2 is surrounded by a jacket of filtered air or helium and is thereafter forced through the nozzle opening of the nozzle 15, having a diameter of 400 $\mu$. In this manner the original diameter of the aerosol stream is decreased by a factor of 5-10.

The aerodynamic focusing has several advantages. It makes possible to provide a very small effective measuring volume 5 which is indispensable for measurements in case of high concentrations. It further provides for a constant particle velocity in the measuring field and also, it prevents circulations of particles within the measuring volume 5. for drawing the aerosol, a constant pressure difference is set between the spectrometer inlet and the measuring volume. This may be obtained with high precision by means of a circulating system (not shown) which is formed of a pump as well as various valves and filters and also includes the airtight recpetacle 11 defining the measuring chamber 12, in the center of which there is arranged the optical measuring field. By including the components 11, 12 into the air circuit, they are continuously rinsed with filtered air. The pressure difference may be indicated by a pressure gauge accurately settable to 1 mm water column pressure. For the aerodynamic focusing dried and filtered pressurized air is used. The flow rate of the jacket air may be set and monitored by means of a flow meter.

It will be understood that the above description of the present invention is susceptible to various modifications, changes and adaptations, and the same are intended to be comprehended within the meaning and range of equivalents of the appended claims.

What is claimed is:

1. In an ultramicroscopic spectrometer for examining properties of aerosol particles, including a receptacle having a wall defining a measuring chamber; an aerosol jet generating means for forming an aerosol jet from the particles by aerodynamic focusing; a mount supporting the aerosol generating means in the measuring chamber; a first passage means supported in the receptacle wall for passing an incident illuminating beam through the receptacle wall into the measuring chamber; an astigmatic image forming system supported in said first passage means for focusing the illuminating beam in the measuring field; a second passage means supported in the receptacle wall for passing an information beam of the aerosol jet through the receptacle wall from the measuring chamber; the axes of the illuminating beam, the information beam and the aerosol jet intersecting in a measuring field in the measuring chamber; the improvement comprising (a) a base defining the bottom of said receptacle and including means defining an opening in said base;
(b) a mount adjusting device arranged adjacent said base externally of said measuring chamber;
(c) a first flexible sealing sleeve projecting through said opening and being secured to said base;
(d) a post passing through said opening and being surrounded by said first flexible sealing sleeve; said post being in circumferential contact with said first flexible sealing sleeve, whereby said first flexible sealing sleeve provides for a sealed penetration of said post into said measuring chamber; said post being further attached to said mount in said measuring chamber and to said mount adjusting device externally of said measuring chamber, whereby said mount can be adjusted by said mount adjusting device during examination of the aerosol particles in said measuring chamber;

(e) a second flexible sealing sleeve projecting through an aperture in said receptacle wall and being secured thereto;

(f) a tube passing through said aperture in said receptacle wall and projecting into said measuring chamber for directing said information beam thereinto; said tube being surrounded by said second flexible sealing sleeve and being in circumferential contact therewith, whereby said second flexible sealing sleeve provides for a sealed penetration of said tube into said measuring chamber; said tube being included in said second passage means and having a microscope objective extending into said measuring chamber; and (g) a tube adjusting device arranged externally of said measuring chamber and being operatively connected to said tube for adjusting said tube and said microscope objective by said tube adjusting device during examination of the aerosol particles in said measuring chamber.

* * * * *